(12) United States Patent
Tsutsumi

(10) Patent No.: US 6,509,182 B2
(45) Date of Patent: Jan. 21, 2003

(54) LIPOLYTIC ENZYMES

(75) Inventor: Noriko Tsutsumi, Chiba-ken (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/892,074

(22) Filed: Jun. 26, 2001

(65) Prior Publication Data

US 2002/0142434 A1 Oct. 3, 2002

Related U.S. Application Data

(60) Provisional application No. 60/215,265, filed on Jun. 30, 2000.

(30) Foreign Application Priority Data

Jun. 26, 2000 (DK) ........................................ 2000 00990
Aug. 4, 2000 (DK) ........................................ 2000 01172

(51) Int. Cl.$^7$ .............................. C12N 9/20; C11D 9/04
(52) U.S. Cl. ...................... 435/198; 510/109; 426/549; 536/23.2
(58) Field of Search .......................... 435/198; 510/109; 426/549; 536/23.2

(56) References Cited

PUBLICATIONS

Shimada et al., Journal of Fermentation and Bioengineering, vol. 75, No. 5 349–352, 1993.
Nagao et al., J. Biochem. 116, 536–540 (1994).
Roberts et al., Mycologia, 79(2), 1987, pp. 265–273, 1987.
Satyanarayana, T. et al., Current Science, vol. 50, No. 15, 1981.

*Primary Examiner*—Nashaat T. Nashed
(74) *Attorney, Agent, or Firm*—Jason I. Garbell

(57) ABSTRACT

The present invention relates to lipolytic enzymes and DNA sequences encoding same. More specifically, the present invention relates to the lipolytic enzyme and DNA encoding same isolated from *Acremonium berkeleyanum* CBS 301.38 and analogues thereof.

6 Claims, No Drawings

SEQUENCE LISTING

<160> NUMBER OF SEQ ID NOS: 20

<210> SEQ ID NO 1
<211> LENGTH: 1103
<212> TYPE: DNA
<213> ORGANISM: Acremonium sp.
<220> FEATURE:
<221> NAME/KEY: CDS
<222> LOCATION: (1)..(85)
<223> OTHER INFORMATION:
<221> NAME/KEY: mat_peptide
<222> LOCATION: (85)..()
<223> OTHER INFORMATION:
<221> NAME/KEY: CDS
<222> LOCATION: (141)..(306)
<223> OTHER INFORMATION:
<221> NAME/KEY: CDS
<222> LOCATION: (365)..(1100)
<223> OTHER INFORMATION:

<400> SEQUENCE: 1

```
atg ctc gcc cta tcc ctt ctt tct att gct gcc ctg gcg gta gct agt        48
Met Leu Ala Leu Ser Leu Leu Ser Ile Ala Ala Leu Ala Val Ala Ser
        -25                 -20                 -15 ccc ttg gcc gat tat tcc aag gcc ttg gaa gac cga g gtgagtccaa            95
Pro Leu Ala Asp Tyr Ser Lys Ala Leu Glu Asp Arg
        -10                 -5                  -1 ccacttacag acctccaggc agaaacgatt gctaagtaaa cacag cc  atc tcg gtc      151
                                                     Ala Ile Ser Val acc gat gga gac ctg aac aac ttc aag ttc tac gtc caa cac gct gcc        199
Thr Asp Gly Asp Leu Asn Asn Phe Lys Phe Tyr Val Gln His Ala Ala
5               10                  15                  20 gcc gca tac tgc aat gtc aac act cca gcg ggt caa gct gtg aag tgc        247
Ala Ala Tyr Cys Asn Val Asn Thr Pro Ala Gly Gln Ala Val Lys Cys
            25                  30                  35 ggc gga tcc aca tgc tct gct gtc gaa ggc gac agg gtg aca gtc gtc        295
Gly Gly Ser Thr Cys Ser Ala Val Glu Gly Asp Arg Val Thr Val Val
        40                  45                  50 gca tcc ttc aa  gtacgttcct cttctatgtt agacttaaag aagcaatccc            346
Ala Ser Phe Asn
        55 agctaacgtc cccatcag c ggc gct gga aca gga att ggc ggc tat gta gcc      398
                      Gly Ala Gly Thr Gly Ile Gly Gly Tyr Val Ala
                              60                  65 acc gac aac gcc cgc tct gag atc gtt gtc tcc atc cgc ggt agt agc        446
Thr Asp Asn Ala Arg Ser Glu Ile Val Val Ser Ile Arg Gly Ser Ser
        70                  75                  80 aat atc cgc aac tgg att gcc aac ata gag ttt gcg cag cag gac tgc        494
Asn Ile Arg Asn Trp Ile Ala Asn Ile Glu Phe Ala Gln Gln Asp Cys
85                  90                  95 tcc ctt gtt gct ggc tgc ggt gtg cac act ggc ttc cag aag gca tgg        542
Ser Leu Val Ala Gly Cys Gly Val His Thr Gly Phe Gln Lys Ala Trp
100                 105                 110                 115 aac gag atc tcc gcc aac gtc aag gcc gct gtg gca tct gcg aag cag        590
Asn Glu Ile Ser Ala Asn Val Lys Ala Ala Val Ala Ser Ala Lys Gln
                120                 125                 130 gcg aac cca agc tac aag atc atc tcg act ggt cac tcc ctc ggc ggt        638
Ala Asn Pro Ser Tyr Lys Ile Ile Ser Thr Gly His Ser Leu Gly Gly
            135                 140                 145 gcg gtg gct acc ctc gcg gcc gcg tac ctg cgt aag gat ggc aat gct        686
Ala Val Ala Thr Leu Ala Ala Ala Tyr Leu Arg Lys Asp Gly Asn Ala
        150                 155                 160
```

```
gtc gat ctg tac aca tac ggc tcg cca cga gtc ggc aac ggt gtc ttc      734
Val Asp Leu Tyr Thr Tyr Gly Ser Pro Arg Val Gly Asn Gly Val Phe
    165                 170                 175 tct aac ttc gtc agc caa caa gcc ggt tct gaa ttc cgc gtc acc cac      782
Ser Asn Phe Val Ser Gln Gln Ala Gly Ser Glu Phe Arg Val Thr His
180                 185                 190                 195 ggc gac gac ccc gtc ccc cgt ctg ccc cca atc gtc ttc ggc tac cgc      830
Gly Asp Asp Pro Val Pro Arg Leu Pro Pro Ile Val Phe Gly Tyr Arg
                200                 205                 210 cac acc acc ccg gag tac tgg ctc gac ggc ggc tcc ctg gac gtg acg      878
His Thr Thr Pro Glu Tyr Trp Leu Asp Gly Gly Ser Leu Asp Val Thr
            215                 220                 225 tac aac ctc gac gag atc aag gtg tgc gag ggc aat gcg aat gtg aac      926
Tyr Asn Leu Asp Glu Ile Lys Val Cys Glu Gly Asn Ala Asn Val Asn
        230                 235                 240 tgc aac ggt ggt acg ttt ggc ctt gat atc ctt gcg cat ttg cgg tac      974
Cys Asn Gly Gly Thr Phe Gly Leu Asp Ile Leu Ala His Leu Arg Tyr
    245                 250                 255 cta cag gat gta tca ggt tgt gcg ccg atc ggc atc ttc tgg aag cgc     1022
Leu Gln Asp Val Ser Gly Cys Ala Pro Ile Gly Ile Phe Trp Lys Arg
260                 265                 270                 275 gag gag atg tcg gat gaa gag ttg gag aag aag gtg aat gag tat gtc     1070
Glu Glu Met Ser Asp Glu Glu Leu Glu Lys Lys Val Asn Glu Tyr Val
                280                 285                 290 cag gcc gac aag gac ttt gtg gct ggg ttg tag                          1103
Gln Ala Asp Lys Asp Phe Val Ala Gly Leu
            295                 300

<210> SEQ ID NO 2
<211> LENGTH: 329
<212> TYPE: PRT
<213> ORGANISM: Acremonium sp.

<400> SEQUENCE: 2

Met Leu Ala Leu Ser Leu Leu Ser Ile Ala Ala Leu Ala Val Ala Ser
         -25                 -20                 -15

Pro Leu Ala Asp Tyr Ser Lys Ala Leu Glu Asp Arg Ala Ile Ser Val
        -10                  -5                  -1   1

Thr Asp Gly Asp Leu Asn Asn Phe Lys Phe Tyr Val Gln His Ala Ala
 5                  10                  15                  20

Ala Ala Tyr Cys Asn Val Asn Thr Pro Ala Gly Gln Ala Val Lys Cys
             25                  30                  35

Gly Gly Ser Thr Cys Ser Ala Val Glu Gly Asp Arg Val Thr Val Val
             40                  45                  50

Ala Ser Phe Asn Gly Ala Gly Thr Gly Ile Gly Gly Tyr Val Ala Thr
         55                  60                  65

Asp Asn Ala Arg Ser Glu Ile Val Ser Ile Arg Gly Ser Ser Asn
 70                  75                  80

Ile Arg Asn Trp Ile Ala Asn Ile Glu Phe Ala Gln Gln Asp Cys Ser
 85                  90                  95                 100

Leu Val Ala Gly Cys Gly Val His Thr Gly Phe Gln Lys Ala Trp Asn
             105                 110                 115

Glu Ile Ser Ala Asn Val Lys Ala Val Ala Ser Ala Lys Gln Ala
             120                 125                 130

Asn Pro Ser Tyr Lys Ile Ile Ser Thr Gly His Ser Leu Gly Gly Ala
         135                 140                 145

Val Ala Thr Leu Ala Ala Ala Tyr Leu Arg Lys Asp Gly Asn Ala Val
```

-continued

```
              150                 155                 160
Asp Leu Tyr Thr Tyr Gly Ser Pro Arg Val Gly Asn Gly Val Phe Ser
165                 170                 175                 180

Asn Phe Val Ser Gln Gln Ala Gly Ser Glu Phe Arg Val Thr His Gly
                185                 190                 195

Asp Asp Pro Val Pro Arg Leu Pro Pro Ile Val Phe Gly Tyr Arg His
                200                 205                 210

Thr Thr Pro Glu Tyr Trp Leu Asp Gly Gly Ser Leu Asp Val Thr Tyr
                215                 220                 225

Asn Leu Asp Glu Ile Lys Val Cys Glu Gly Asn Ala Asn Val Asn Cys
            230                 235                 240

Asn Gly Gly Thr Phe Gly Leu Asp Ile Leu Ala His Leu Arg Tyr Leu
245                 250                 255                 260

Gln Asp Val Ser Gly Cys Ala Pro Ile Gly Ile Phe Trp Lys Arg Glu
                265                 270                 275

Glu Met Ser Asp Glu Glu Leu Glu Lys Lys Val Asn Glu Tyr Val Gln
                280                 285                 290

Ala Asp Lys Asp Phe Val Ala Gly Leu
            295                 300

<210> SEQ ID NO 3
<211> LENGTH: 23
<212> TYPE: PRT
<213> ORGANISM: Artificial Sequence
<220> FEATURE:
<223> OTHER INFORMATION: Primer

<400> SEQUENCE: 3

Cys Ala Arg Cys Ala Tyr Gly Gly Ile Gly Cys Ile Gly Cys Ile Gly
1               5                   10                  15

Cys Ile Thr Ala Tyr Thr Gly
            20

<210> SEQ ID NO 4
<211> LENGTH: 23
<212> TYPE: PRT
<213> ORGANISM: Artificial Sequence
<220> FEATURE:
<223> OTHER INFORMATION: Primer

<400> SEQUENCE: 4

Ala Ala Ile Cys Cys Ile Ile Ile Arg Thr Gly Ile Ala Cys Ile Cys
1               5                   10                  15

Cys Arg Cys Ala Ile Cys Cys
            20

<210> SEQ ID NO 5
<211> LENGTH: 23
<212> TYPE: PRT
<213> ORGANISM: Artificial Sequence
<220> FEATURE:
<223> OTHER INFORMATION: Primer

<400> SEQUENCE: 5

Gly Gly Ile Thr Gly Tyr Gly Gly Ile Gly Thr Ile Cys Ala Tyr Ile
1               5                   10                  15

Ile Ile Gly Gly Ile Thr Thr
            20

<210> SEQ ID NO 6
```

-continued

```
<211> LENGTH: 23
<212> TYPE: PRT
<213> ORGANISM: Artificial Sequence
<220> FEATURE:
<223> OTHER INFORMATION: Synthetic

<400> SEQUENCE: 6

Thr Cys Ile Ser Trp Ile Gly Thr Tyr Thr Gly Ile Cys Lys Arg Thr
1               5                  10                  15

Ala Ile Cys Cys Arg Ala Ala
            20

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
tggatccgcc gcacttcaca gcttgacccg                                    30

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
cggcaacggt gtcttctcta acttcgtcag cc                                 32

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
tattatcatg atcaatgctc gccctatccc ttctttct                           38

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
ccgctcgagc tacaacccag ccacaaagtc cttgtc                             36

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
ttgaattgaa aatagattga tttaaaactt c                                  31

<210> SEQ ID NO 12
<211> LENGTH: 25
<212> TYPE: DNA
<213> ORGANISM: Artificial Sequence
```

```
<220> FEATURE:
<223> OTHER INFORMATION: Primer

<400> SEQUENCE: 12
ttgcatgcgt aatcatggtc atagc                                    25

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
ttgaattcat gggtaataac tgatat                                   26

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14
aaatcaatct attttcaatt caattcatca tt                            32

<210> SEQ ID NO 15
<211> LENGTH: 11
<212> TYPE: DNA
<213> ORGANISM: Aspergillus

<400> SEQUENCE: 15
gtactaaaac c                                                   11

<210> SEQ ID NO 16
<211> LENGTH: 11
<212> TYPE: DNA
<213> ORGANISM: Artificial Sequence
<220> FEATURE:
<223> OTHER INFORMATION: Synthetic

<400> SEQUENCE: 16
ccgttaaatt t                                                   11

<210> SEQ ID NO 17
<211> LENGTH: 45
<212> TYPE: DNA
<213> ORGANISM: Artificial Sequence
<220> FEATURE:
<223> OTHER INFORMATION: Primer

<400> SEQUENCE: 17
ggatgctgtt gactccggaa atttaacggt ttggtcttgc atccc              45

<210> SEQ ID NO 18
<211> LENGTH: 14
<212> TYPE: DNA
<213> ORGANISM: Aspergillus

<400> SEQUENCE: 18
atgcaattta aact                                                14

<210> SEQ ID NO 19
<211> LENGTH: 14
<212> TYPE: DNA
```

```
<213> ORGANISM: Artificial Sequence
<220> FEATURE:
<223> OTHER INFORMATION: Synthetic

<400> SEQUENCE: 19
cggcaattta acgg                                                          14

<210> SEQ ID NO 20
<211> LENGTH: 44
<212> TYPE: DNA
<213> ORGANISM: Artificial Sequence
<220> FEATURE:
<223> OTHER INFORMATION: Primer

<400> SEQUENCE: 20
ggtattgtcc tgcagacggc aatttaacgg cttctgcgaa tcgc                         44
```

LIPOLYTIC ENZYMES

CROSS-REFERENCE TO RELATED APPLICATIONS

This application claims under 35 U.S.C. 119 priority from Danish application Nos. PA 2000 00990, filed Jun. 26, 2000, and PA 2000 01172, filed Aug. 4, 2000, and the benefit of U.S. provisional application No. 60/215265, filed Jun. 30, 2000, the contents of which are fully incorporated herein by reference.

FIELD OF THE INVENTION

The present invention relates to lipolytic enzymes, methods of using and producing lipolytic enzymes, as well as nucleic acid sequence encoding same.

BACKGROUND OF THE INVENTION

Lipolytic enzymes (such as lipases and phospholipases) are capable of hydrolyzing carboxylic ester bonds in a substrate to release carboxylic acids. They are known to be useful, e.g., in baking and detergents.

A lipase from *Fusarium heterosporum* and its sequence are known. Journal of Fermentation and Bioengineering, 75 (5), p 349–352, 1993. Journal of Biochemistry (Tokyo), 116 (3), p 536–540, 1994.

Some isolates of Acremonium are known to produce lipase. Roberts et al., Mycologia, 79, 265–273, 1987. Satyanarayana & Johri, Current Science, 50, 680–682, 1981.

SUMMARY OF THE INVENTION

The inventors have isolated a lipolytic enzyme from a strain of *Acremonium berkeleyanum*. The inventors also isolated the gene encoding the novel lipolytic enzyme and cloned it into an *E. coli* strain.

Accordingly, the invention provides a lipolytic enzyme which may be a polypeptide having an amino acid sequence as the mature peptide shown in SEQ ID NO: 1.

Further, the lipolytic enzyme of the invention may be a polypeptide encoded by the lipolytic enzyme encoding part of the DNA sequence cloned into a plasmid present in *Escherichia coli* deposit number DSM 13538.

The lipolytic enzyme may also be an analogue of the polypeptide defined above which:

i) has at least 70% homology with said polypeptide,
ii) is immunologically reactive with an antibody raised against said polypeptide in purified form,
iii) is an allelic variant of said polypeptide, The lipolytic enzyme of the invention may also be a polypeptide which is encoded by a nucleic acid sequence which hybridizes under high stringency conditions with a complementary strand of the nucleic acid sequence of SEQ ID NO: 1 encoding the mature polypeptide or a subsequence thereof having at least 100 nucleotides.

The nucleic acid sequence of the invention may comprise a nucleic acid sequence which encodes the lipolytic enzyme described above. The nucleic acid sequence may also comprise:

a) the DNA sequence encoding a mature lipolytic enzyme cloned into a plasmid present in *Escherichia coli* DSM 13538,
b) the DNA sequence encoding a mature lipolytic enzyme shown in SEQ ID NO: 1, or
c) an analogue of the DNA sequence defined in a) or b) which i) has at least 70% homology with said DNA sequence, or
ii) hybridizes at high stringency with said DNA sequence, its complementary strand or a subsequence thereof.

Other aspects of the invention provide a recombinant expression vector comprising the DNA sequence, and a cell transformed with the DNA sequence or the recombinant expression vector.

A comparison with full-length prior-art sequences shows that the mature amino acid sequence of the invention has 67% homology with the lipase from *Fusarium heterosporum* described above, and the corresponding DNA sequence of the invention shows 68% homology with that of the F. heterosporum enzyme.

DETAILED DESCRIPTION OF THE INVENTION

Genomic DNA Source

A lipolytic enzyme of the invention may be derived from a strain of Acremonium, particularly *A. berkeleyanum*, using probes designed on the basis of the DNA sequences in this specification. One such strain is *A. berkeleyanum* CBS 301.38, publicly available from Centraalbureau voor Schimmelcultures, Baarn-Delft, the Netherlands.

A strain of *Escherichia coli* containing a gene encoding lipolytic enzyme was deposited by the inventors under the terms of the Budapest Treaty with the DSMZ-Deutshe Sammmlung von Microorganismen und Zelikulturen GmbH, Mascheroder Weg 1b, D-38124 Braunschweig DE, Germany. The deposit date was Jun. 15, 2000, and the accession number was DSM 13538.

Properties of Lipolytic Enzyme

The lipolytic enzyme is able to hydrolyze carboxylic ester bonds and is classified as EC 3.1.1 according to Enzyme Nomenclature 1992, Academic Press, Inc. The enzyme has lipase (triacylglycerol lipase) activity (EC 3.1.1.3) and may also have phospholipase activity.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lipolytic enzyme of the invention may be produced by transforming a suitable host cell with a DNA sequence encoding the lipolytic enzyme, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, e.g. a strain of Aspergillus, Fusarium, Trichoderma or Saccharomyces, particularly *A. niger, A. oryzae, F. graminearum, F. sambucinum, F. cerealis* or *S. cerevisiae*. The production of the lipolytic enzyme in such host organisms may be done by the general methods described in EP 238,023 (Novo Nordisk), WO 96/00787 (Novo Nordisk) or EP 244,234 (Alko).

Hybridization

The hybridization is used to indicate that a given DNA sequence is analogous to a nucleotide probe corresponding to a DNA sequence of the invention. The hybridization conditions are described in detail below.

Suitable conditions for determining hybridization between a nucleotide probe and a homologous DNA or RNA sequence involves presoaking of the filter containing the DNA fragments or RNA to hybridize in 5× SSC (standard saline citrate) for 10 min, and prehybridization of the filter in a solution of 5× SSC (Sambrook et al. 1989), 5× Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity >1×10$_9$ cpm/µg) probe for 12 hours at approx. 45° C. The filter is then washed two times for 30 minutes in 2× SSC, 0.5% SDS at a temperature of at least 55° C., more preferably at least 60° C., more preferably at least 65° C., even more preferably at least 70° C., especially at least 75° C.

Molecules to which the oligonucleotide probe hybridizes under these conditions are detected using an x-ray film.

Alignment and Homology

The present invention also includes lipolytic enzymes and nucleotide sequences encoding same that have homology to the disclosed sequences. More preferably, the lipolytic enzymes and the nucleotide sequences of the invention may have homologies to the disclosed sequences of at least 70%, at least 80%, at least 85%, at least 90% or at least 95%, e.g. at least 96%, at least 97%, at least 98%.

For purposes of the present invention, alignments of sequences and calculation of homology scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA", Methods in Enzymology, 183:63–98).

Lipase Activity (LU)

A substrate for lipase is prepared an emulsion of 5% by volume of tributyrin (glycerin tributyrate) using 0.1% gum Arabic as emulsifier. The hydrolysis of tributyrin at 30° C. at pH 7 is followed in a pH-stat titration experiment. One unit of lipase activity (1 LU) equals the amount of enzyme capable of releasing 1 µmol butyric acid/min at the standard conditions. 1 KLU=1000 LU.

Use of Lipolytic Enzyme

The lipolytic enzyme of the invention can be used in various industrial application of lipolytic enzymes, e.g. in baking, detergents, diglyceride synthesis (EP 307154), acidolysis, interesterification (WO 8802775), ester hydrolysis, oil degumming (JP-A 2-153997, U.S. Pat. No. 5,264,367), production of lysolecithin (JP patent 2794574, JP-B 6-087751) and in the process described in PCT/DK 00/00109.

Use in Baking

The lipolytic enzyme of the invention can be used in the preparation of dough, bread and cakes, e.g. to improve the elasticity of the bread or cake. Thus, the lipolytic enzyme can be used in a process for making bread, comprising adding the lipolytic enzyme to the ingredients of a dough, kneading the dough and baking the dough to make the bread. This can be done in analogy with WO 9404035 and EP 585988.

Use in Detergent

The variant may be used as a detergent additive, e.g. at a concentration (expressed as pure enzyme protein) of 0.001–10 (e.g. 0.01–1) mg per gram of detergent or 0.001–100 (e.g. 0.01–10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK WO 98/08939 and WO 97/43375.

The detergent composition of the invention may particularly be formulated for hand or machine dishwashing operations. e.g. as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

MATERIALS AND METHODS

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for Bacillus". John Wiley and Sons, 1990.

Enzymes

Enzymes for DNA manipulations (e.g. restriction endonucleases, ligases etc.) are obtainable from New England Biolabs, Inc. and were used according to the manufacturer's instructions.

Plasmids/Vectors pT7Blue (Invitrogen, Netherlands)

Cloning

LA PCR™ in vitro Cloning Kit (TaKaRa) was used for cloning and was used according to the manufacturer's instructions.

Microbial Strains

E. coli JM109 (TOYOBO, Japan)

E. coli JM110 (Invitrogen)

E. coliDB6507 (F,pnrF74::Tn5,seupE44, lacY1, ara-14, galK2, xyl-5, mtl-1,leuB6, proA2, hsdS20, recA13, rpsL20, thi-1, lambda-)

A. oryzae BECh-2 is described in Danish patent application PA 1999 01726. It is a mutant of JaL 228 (described in WO 98/12300) which is a mutant of IFO 4177.

Reagents
Media and Reagents
Cove: 342.3 g/L Sucrose, 20 ml/L COVE salt solution, 10 mM Acetamide, 30 g/L noble agar.
Cove-2: 30 g/L Sucrose, 20 ml/L COVE salt solution, 10 mM, Acetamide, 30 g/L noble agar.
Cove salt solution: per liter 26 g KCl, 26 g MgSO4–7aq, 76 g KH2PO4, 50ml Cove trace metals.
Cove trace metals: per liter 0.04 g NaB407–10aq, 0.4 g CuSO4–5aq, 1.2 g FeSO4–7aq, 0.7 g MnSO4-aq, 0.7 g Na2MoO2-2aq, 0.7 g ZnSO4–7aq.
AMG trace metals: per liter 14.3 g ZnSO4–7aq, 2.5 g CuSO4–5aq, 0.5 g NiCl2, 13.8 g FeSO4, 8.5 g MnSO4, 3.0 g citric acid.
YPG: 4 g/L Yeast extract, 1 g/L KH2PO4, 0.5 g/L MgSO4–7aq, 5 g/L Glucose, pH 6.0.
STC: 0.8 M Sorbitol, 25 mM Tris pH 8, 25 mM CaCl2.
STPC: 40% PEG4000 in STC buffer.
Cove top agarose: 342.3 g/L Sucrose, 20 ml/L COVE salt solution, 10 mM Acetamide, 10 g/L low melt agarose.
MS-9: per liter 30 g soybean powder, 20 g glycerol, pH 6.0.
MDU-pH5: per liter 45 g maltose-1aq, 7 g yeast extract, 12 g KH2PO4, 1 g MgSO4–7aq, 2 g K2SO4, 0.5 ml AMG trace metal solution and 25 g 2-morpholinoethanesulfonic acid, pH 5.0.

EXAMPLES

Example 1

Cloning and Expression of Lipase Gene from Acremonium Berkeley-anum

Transformation in Aspergillus Strain

*Aspergillus oryzae* strain BECh-2 was inoculated to 100 ml of YPG medium and incubated for16 hrs at 32° C. at 120 rpm. Pellets were collected and washed with 0.6 M KCl, and resuspended 20 ml 0.6 M KCl containing a commercial β-glucanase product (Glucanex, product of Novo Nordisk A/S) at the concentration of 30 μl/ml. Cultures were incubated at 32° C. at 60 rpm until protoplasts formed, then washed with STC buffer twice. The protoplasts were counted with a hematometer and resuspended in an 8:2:0.1 solution of STC:STPC:DMSO to a final concentration of 2.5×10e7 protoplasts/ml. About 3 μg of DNA was added to 100 μl of protoplasts solution, mixed gently and incubated on ice for 30 min. One ml of SPTC was added and incubated 30 min at 37° C. After the addition of 10 ml of 50° C. Cove top agarose, the reaction was poured onto Cove agar plate. Transformation plates were incubated at 32° C. for 5 days.

PCR Screening of Lipase

PCR reactions on *Acremonium berkeleyanum* genomic DNA was done with two following primer sets: lip3/lip11 and lip10/lip21 designed based upon the alignment 3 lipases from Fusarium.

lip3: 5'-carcayggigcigcigcitaytg-3' (SEQ ID NO:3)

lip 11: 5'-aaicciiirtgiaciccrcaicc-3' (SEQ ID NO:4)

lip10: 5'-ggitgyggigticayiiiggift-3' (SEQ ID NO:5)

lip21: 5'-tciswigtytgickrtaiccraa-3' (SEQ ID NO:6)

Reaction components (2.5 ng /μl of genomic DNA, 250 mM dNTP each, primer 250 nM each, 0.1 U/μl in Taq polymerase in 1× buffer (Roche Diagnostics, Japan)) were mixed and submitted for PCR under the following conditions.

| Step | Temperature | Time |
| --- | --- | --- |
| 1 | 94° C. | 1 min |
| 2 | 50° C. | 1 min |
| 3 | 72° C. | 2 min |
| 4 | 72° C. | 10 min |
| 5 | 4° C. | forever |

Steps 1 to 3 were repeated 30 times.

340 bp of fragment and 330 bp of fragment were amplified from primer sets of lip3/lip11 and lip10/lip21, respectively. They were gel-purified with GFX™ PCR DNA and Gel Band Purification kit (amersham pharmacia biotech) and ligated into a pT7Blue vector with ligation high (TOYOBO, Japan). The ligation mixtures were transformed into *E. coli* JM109. The resultant plasmids, pTAc-0310 and pTAc-1021, were sequenced and compared to the *Fusarium oxysporum* lipase, showing that a clone encodes the internal part of the lipase.

Cloning of Lipase Gene

In order to clone the missing part of the lipase gene, LA PCR™ in vitro Cloning Kit (TaKaRa) was used for genome walking. One kb of DNA fragment corresponding to N-terminal region was obtained from Sal I digested genome ligated to Sal I cassette of the kit with AcN3 primer. One kb of DNA fragment corresponding to C-terminal region was obtained from Hind III digested genome ligated to Hind III cassette of the kit with AcC3 primer.

AcN3: tggatccgccgcacttcacagcttgacccg (SEQ ID NO:7)

AcC3: cggcaacggtgtcttctctaacttcgtcagcc (SEQ ID NO:8)

Obtained fragments were purified by GFX™ PCR DNA and Gel Band Purification kit (amersham pharmacia biotech) and sequenced with each primer which amplified the fragment. The sequences were compared to *Fusarium oxysporum* lipase, showing that an amplified DNA fragments encodes the whole part of lipase.

The fidelity of taq polymerase is not good so in order to get the right sequence whole gene was amplified the following primers.

152-N (Bcl): 5'-tattatcatgatcaatgctcgccctatcccttctttct-3' (SEQ ID NO:9)

152-C(Xho): 5'-ccgctcgagctacaacccagccacaaagtccttgtc-3' (SEQ ID NO:10)

Reaction components (6 ng /μl of genomic DNA, 250 mM dNTP each, primer 250 nM each, 0.05 U/μl of Expand high fidelity polymerase in 1×buffer (Roche Diagnostics, Japan)) were mixed and submitted for PCR under the following conditions.

| Step | Temperature | Time |
| --- | --- | --- |
| 1 | 94° C. | 2 min |
| 2 | 94° C. | 10 sec |
| 3 | 55° C. | 30 sec |
| 4 | 68° C. | 45 sec |
| step 2–4 repeat 10 times | | |
| 5 | 94° C. | 10 sec |
| 6 | 55° C. | 30 sec |
| 7 | 68° C. | 45 sec |
| | | +20 sec/cycle |

| Step | Temperature | Time |
|---|---|---|
| | step 5–7, repeat 20 times | |
| 8 | 68° C. | 7 min |
| 7 | 4° C. | forever |

Amplified DNA fragment was gel-purified with GFX™ PCR DNA and Gel Band Purification kit (amersham pharmacia biotech) and ligated into a pT7Blue vector with ligation high (TOYOBO, Japan). The ligation mixtures were transformed into *E. coli* JM109. The resultant plasmids, pT152-1 and pT152-2, were sequenced and they are identical. pT152-1 sequence is defined as *Acremonium berkeleyanum* lipase nucleotide sequence.

Construction of Expression Plasmid pMT 2188.

*Aspergillus oryzae* expression plasmid pCaHj 483 (described in WO 98/00529) consists of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid is the Aspergillus selective marker amdS from *Aspergillus nidulans* enabling growth on acetamide as sole nitrogen source. These elements were cloned into the *E. coli* vector pUC19. The ampicillin resistance marker enabling selection in *E. coli* of this plasmid was replaced with the URA3 marker of *Saccharomyces cerevisiae* that can complement a pyrF mutation in *E. coli* in the following way:

The pUC19 origin of replication was PCR amplified from pCaHj483 with the primers:

142779: TTG MT TGA AAA TAG ATT GAT TTA AAA CTT C (SEQ ID NO:11)

142780: TTG CAT GCG TM TCA TGG TCA TAG C (SEQ ID NO:12)

The primer 142780 introduces a Bbu I site in the PCR fragment.

The Expand PCR system (Roche Molecular Biochemicals, Basel, Switserland) was used for the amplification following the manufacturers instructions for this and the subsequent PCR amplifications.

The URA3 gene was amplified from the general *S. cerevisiae* cloning vector pYES2 (Invitrogen corporation, Carlsbad, Calif., USA) using the primers:

140288: TTG MT TCA TGG GTA ATA ACT GAT AT (SEQ ID NO:13)

142778: AAA TCA ATC TAT TTT CAA TTC MT TCA TCA TT (SEQ ID NO:14)

The primer 140288 introduces an EcoR I site in the PCR fragment.

The two PCR fragments were fused by mixing them and amplifying using the primers 142780 and 140288 using the splicing by overlap method (Horton et al (1989) Gene, 77, 61–68).

The resulting fragment was digested with EcoR I and Bbu I and ligated to the largest fragment of pCaHj 483 digested with the same enzymes. The ligation mixture was used to transform the pyrFp *E. coli* strain DB6507 (ATCC 35673) made competent by the method of Mandel and Higa (Mandel, M. and A. Higa (1970) J. Mol. Biol. 45, 154). Transformants were selected on solid M9 medium (Sambrook et. al (1989) Molecular cloning, a laboratory manual, 2. edition, Cold Spring Harbor Laboratory Press) supplemented with 1 g/l casaminoacids, 500 µg/l thiamine and 10 mg/l kanamycin.

A plasmid from such a transformant was termed pCaHj 527.

The Pna2/tpi promoter present on pCaHj527 was subjected to site directed mutagenises by a simple PCR approach.

Nucleotide 134–144 was altered from GTACTAAAACC (SEQ ID NO:15) to CCGTTAAATTT (SEQ ID NO:16) using the mutagenic primer 141223:

141223: GGA TGC TGT TGA CTC CGG AAA TTT MC GGT TTG GTC TTG CAT CCC (SEQ ID NO:17).

Nucleotide 423–436 was altered from ATGCMTT-TAAACT (SEQ ID NO:18) to CGGCMTTTAACGG (SEQ ID NO:19) using the mutagenic primer 141222:

141222: GGT ATT GTC CTG CAG ACG GCA ATT TM CGG CTT CTG CGA ATC GC (SEQ ID NO:20).

The resulting plasmid was termed pMT 2188.

Expression of Lipase Gene in Aspergillus Oryzae.

The plasmid pT152-1 was transformed to JM110 and non-methylated pT152-1 was extracted. The lipase gene was digested from non-methylated pT152-1 with Bcl I and Xho I and ligated into the BamH I and XhoI sites in the Aspergillus expression cassette pMT2188 which has *Aspergillus niger* neutral amylase promoter, *Aspergillus nidulans* TPI leader sequences, *Aspergillus niger* glucoamylase terminator and *Aspergillus nidulans* amdS gene as a marker and *Saccharomyces cerevisiae* URA3 gene as a marker for a plasmid construction. The ligation mixture was transformed *E. coli* 6507 by electroporation and the resultant plasmid was pNL152-3 (24).

pNL152-3 (24) was transformed into *Aspergillus oryzae* BECh-2. The selected transformants were inoculated in 100 ml of MS-9 media and cultivated at 30° C. for 1 day. 3 ml of grown cell in MS-9 medium was inoculated to 100 ml of MDU-2BP medium and cultivated at 32° C. for 3 days. The supernatant was obtained by centrifugation.

The lipase productivity of selected transformants was determined as LU activity.

SEQUENCE LISTING lip3: 5'-carcayggigcigcigcitaytg-3' (SEQ ID NO:3)

lip11: 5'-aaicciiirtgiaciccrcaicc-3' (SEQ ID NO:4)

lip10: 5'-ggitgyggigticayiiiggitt-3' (SEQ ID NO:5)

lip21: 5'-tciswigtytgickrtaiccraa-3' (SEQ ID NO:6)

AcN3: tggatccgccgcacftcacagcttgacccg (SEQ ID NO:7)

AcC3: cggcaacggtgtcttctctaacttcgtcagcc (SEQ ID NO:8)

152-N (Bcl): 5'-tattatcatgatcaatgctcgccctatcccttctttct-3' (SEQ ID NO:9)

152-C(Xho): 5'-ccgctcgagctacaacccagccacaaagtccttgtc-3' (SEQ ID NO:10)

142779: TTG MT TGA AAA TAG ATT GAT TTA AAA CTT C (SEQ ID NO:11)

142780: TTG CAT GCG TM TCA TGG TCA TAG C (SEQ ID NO:12)

140288: TTG MT TCA TGG GTA ATA ACT GAT AT (SEQ ID NO: 13)

142778: AAA TCA ATC TAT TUI CM TTC MT TCA TCA TT (SEQ ID NO: 14)

141223: GGA TGC TGT TGA CTC CGG AAA TIT MC GGT TTG GTC TTG CAT CCC. (SEQ ID NO:17)

141222: GGT ATT GTC CTG CAG ACG GCA ATT TM CGG CTT CTG CGA ATC GC. (SEQ ID NO:20)

What is claimed is:

1. An isolated lipolytic enzyme, comprising:
   a) a polypeptide encoded by the lipolytic enzyme encoding part of the DNA sequence cloned into a plasmid present in *Escherchia coli* deposit number DSM 13538,
   b) a polypeptide having an amino acid sequence of the mature peptide shown in SEQ ID NO: 2;
   c) an analogue of the polypeptide defined in (a) or (b) which has at least 95% homology with said polypeptide, or
   d) a polypeptide which is encoded by a nucleic acid sequence which hybridizes with a complementary strand of the nucleic acid sequence of SEQ ID NO: 1 encoding the mature polypeptide under hybridization conditions comprising prehybridizing in a solution of 5× SSC, 5 × Denhardt's solution, 0.5% SDS and 100 µg/ml of denatured sonicated salmon sperm DNA, followed by hybridization in the same solution for 12 hours at approx. 45° C., followed by washing in 2× SSC, 0.5% SDS for 30 minutes at a temperature of at least 70° C.

2. The lipolytic enzyme of claim 1 which is native to a strain of Acremonium.

3. The lipolytic enzyme of claim 1 which is native to a strain of *A. berkeieyanum.*

4. A method for preparing a dough or a baked product made from the dough, comprising adding the lipolytic enzyme of claim 1 to the dough.

5. A dough composition comprising the lipolytic enzyme of claim 1.

6. A detergent composition comprising a surfactant and the lipolytic enzyme of claim 1.

\* \* \* \* \*